US006037175A

United States Patent [19]
Cameron et al.

[11] Patent Number: 6,037,175
[45] Date of Patent: *Mar. 14, 2000

[54] METHOD AND MEDIA FOR ENHANCING CRYOPRESERVATION OF CELLS

[75] Inventors: Don F. Cameron, Lutz; Paul R. Sanberg, Springhill; Cesario V. Borlongan, Lutz; Samuel Saporta, Tampa, all of Fla.

[73] Assignee: The University of South Florida, Tampa, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/615,039

[22] Filed: Mar. 12, 1996

[51] Int. Cl.$^7$ ...................................................... A01N 1/02
[52] U.S. Cl. ........................ 435/374; 435/375; 435/1.3; 435/404; 435/406; 435/366
[58] Field of Search ................................. 435/404, 406, 435/366, 1.3, 375, 374

[56] References Cited

U.S. PATENT DOCUMENTS 5,082,670   1/1992   Gage et al. .

FOREIGN PATENT DOCUMENTS

WO9528167   10/1995   WIPO .

OTHER PUBLICATIONS

Selawry et al., "Production of a factor, or factors, suppressing IL–2 production and T cell Proliferation by sertoli cell–enriched Preparations"*Transplantation* 52:846–850 (1991).
Selawry et al, (1991) Transplantation. 52(5): 846–850.
Carson et al., "Synthesis and secretion of a novel binding protein for retinol by a cell line derived from Sertoli Cells" *Journal of Biological Chemistry*, vol. 259, No. 5, pp. 3117–3123 (1984).
Berden et al., "Severe central–nervous system toxicity associated with cyclosporin" *The Lancet* 26:219–220 (1985).
Bjorklund and Stenevi, "Intracerebral neural grafting: A historical perspective" *Neural grafting in the mammalian CNS*, Amsterdam:Elsevier pp. 3–14 (1985).
Bjorklund, "Dopaminergic transplants in experimental parkinsonism: cellular mechanisms of graft–induced functional recovery" Current Biology, 2:683–689 (1992).
Borlorgan et al., "Cyclosporine–a increases spontaneous and dopamine agonist–induced locomotor behavior in normal rats" *Cell Transplantation*, vol. 4, No. 1, pp. 65–73 (1995).
Borlongan et al., "Striatal dopamine–mediated motor behavior is altered following occlusion of the middle cerebral artery" *Pharm. Biochem. and Behavior*, vol. 52, No. 1 pp. 225–229 (1995).
Borlongan et al., "Systemic 3–nitropropionic acid: behavioral deficits and striatal damage in adult rats" *Brain Research Bulletin* vol. 36, No. 6, pp. 549–556 (1995).
Cameron et al., Sertoli cells maintain spermatid viability in vitro" *Cell biology of the testis and epididymis*, vol. 513 Annals of the New York Academy of Sciences, pp. 419–423 (1987a).

Cameron et al., "Alterations of androgen–binding protein (ABP) in sertoli/spermatid cocultures with varying . . . " *Cell biology of the testis and epididymis*, New York Acad. Sci., pp. 448–451 (1987b).
Cameron et al., "Successful islet/abdominal testis transplantation does not require leydig cells[1]" *Transplantation*, vol. 50, No. 4 pp. 649–653 (1990).
Cameron and Muffly, "Hormonal regulation of spermatid binding" *Journal of Cell Science*, 100:623–633 (1991).
de Groen et al., "Central nervous system toxicity after liver transplantation" *The New England Journal of Medicine*, 14:861–866 (1987).
Freeman et al., "The USF protocol for fetal nigral transplantation in Parkinson's Disease" *Experimental Neurology*, 129:6–7 (1994).
Griswold, Protein secretion by sertoli cells: general considerations Russell, L.D. and M.D. Griswold, eds. The Sertoli Cell, Cache River Press, Clearwater, Fl., pp. 195–200 (1992).
Isacson et al., "Graft–induced behavioral recovery in an animal model of huntington disease" *Proc. Natl. Acad. Sci. USA*, vol. 83, pp. 2728–2732 (1986).
Koutouzis et al., "Intrastriatal 3–nitropropionic acid: a behavioral assessment" *NeuroReport*, vol. 5, No. 17 pp. 2241–2245 (1994).
Koutouzis et al., "Systemic 3–nitropropionic acid: long–term effects on locomotor behavior" *Brain Resrarch*, 646:242–246 (1994).
Lindvall et al., "Transplantation in parkinson's disease: two cases of adrenal medullary grafts to the putamen" *Annals of Neurology* vol. 22, No. 4, pp. 457–468 (1987).
Lindvall et al., "Grafts of fetal dopamine neurons survive and improve motor function in parkinson's disease" *Science*, 247:574–577 (1990).
Pakzaban et al., "Increased proportion of acetylcholinesterase–rich zones and improved morphological integration in host striatum of . . . ", *Brain Research*, 97:13–22 (1993).
Sagen et al., "Transplants of Immunologically isolated xenogeneic chromaffin cells provide a long–term source of pain–reducing . . . " *Journal of Neuroscience*, 13:2415–2423 (1993).
Sanberg et al., "Transplantation into the central nervous system" R. G. Landesd Co., Boca Raton, Fl., pp. 19–21 (1994).
Selawry and Cameron, "Sertoli cell–enriched fractions in successful islet cell transplantation" *Cell Transplantation*, vol. 2, No. 3 pp. 123–129 (1993).
Wictorin et al., "Reformation of long axon pathways in adult rat central nervous system by human forebrain neuroblasts" *Nature*, vol. 347, pp. 556–558 (1990).

*Primary Examiner*—Christina Y. Chan
*Assistant Examiner*—Patrick J. Nolan
*Attorney, Agent, or Firm*—Kohn & Associates

[57] ABSTRACT

A method of enhancing the viability of cryopreserved cells is culturing Sertoli cells in media to produce preconditioned media and adding the preconditioned media to the cells to be cryopreserved. The cells are then cryopreserved. Alternatively, a method of enhancing the viability of cryopreserved cells is co-culturing Sertoli cells and cells to be cryopreserved in media and cryopreserving both.

6 Claims, 4 Drawing Sheets

METHOD AND MEDIA FOR ENHANCING CRYOPRESERVATION OF CELLS

TECHNICAL FIELD

The present invention relates to cell viability and, specifically, to methods of enhancing the viability of cryopreserved cells.

BACKGROUND OF THE INVENTION

Transplantation of cells is being utilized therapeutically from bone marrow transplants to neural cell transplants. Improved means to facilitate such cellular transplants are needed, particularly where differentiated cells are being transplanted. These cells cannot be cultured to increase cell number so preservation of viability for transplant is critical.

Transplantation protocols can include the infusion of cells from a donor. For example, in some cancer therapies a patient's bone marrow is removed, and then reinfused following high dose chemo- and/or radiation therapies. It would be useful to have improved methods of preserving such cells. In other cases, bone marrow donors are not available from relatives and must be matched from the national registry. It would be useful to be able to have preserved such cells rather than having to find the donor at the time the cells are needed. Therefore, improved methods of cryopreservation are needed since a substantial portion of cryopreserved cells are not viable upon thawing.

In addition, hybridomas are stored utilizing cryopreservation. Improved methods for preserving hybridomas with increased viability would be useful.

As a further example, the central nervous system (CNS) (brain and spinal cord) has poor regenerative capacity which is exemplified in a number of neurodegenerative disorders. An example of such a disorder is Parkinson's disease. The preferred pharmacotherapy for Parkinson's disease is L-dopa which helps the symptoms of this disease in humans. However, the neuropathological damage and the debilitating progression is not reversed by this treatment protocol.

Laboratory and clinical studies have shown the transplantation of cells into the CNS is a potentially significant alternative therapeutic modality for neurodegenerative disorders such as Parkinson's disease (Wictorin et al., 1990; Lindvall et al., 1990; Sanberg et al., 1994; Bjorklund and Stenevi, 1985; Freeman et al., 1994). In some cases, transplanted neural tissue can survive and form connections with the CNS of the recipient i.e. the host (Wictorin et al., 1990). When successfully accepted by the host, the transplanted tissue (i.e. the graft) has been shown to ameliorate the behavioral deficits associated with the disorder (Sanberg et al., 1994). The obligatory step for the success of this kind of treatment is to have viable cells available for the transplant.

Currently, fetal neural tissue is the primary graft source for neural transplantation (Lindvall et al., 1990; Bjorklund, 1992; Isacson et al., 1986; Sanberg et al., 1994). Other viable graft sources include adrenal chromaffin cells and various cell types that secrete neural growth factors and trophic factors. The field of neural tissue transplantation as a productive treatment protocol for neurodegenerative disorders has received much attention resulting in its progression to clinical trials. Preliminary results and clinical observations are promising but obtaining viable cells remains a problem.

Recently, studies have suggested that Sertoli cells, when simultaneously transplanted with pancreatic islet cell into the diabetic rat, act as an effective local immunosuppressant on the host tissue (Selawry and Cameron, 1993). As a result, the graft is not rejected and the islets remain viable allowing the transplanted β-cells to function normally and produce insulin for an indefinite period of time. As a result, the accepted graft overcomes the primary physiological dysfunction of hyperglycemia thereby alleviating the related complications of this endocrine disorder. This cell transplantation protocol is accomplished without prolonged systemic immunosuppression, otherwise necessary when islets are transplanted without Sertoli cells.

In general, systemic immunosuppression is necessary if successful transplantation is to be achieved in humans. Immunosuppression of the entire body (i.e. systemic) can result, eventually, in graft acceptance. It is acquired, however, by placing the individual at medical risk making the immunosuppressant therapy itself more of a liability than a benefit in some cases. For a lack of a better immunosuppressant treatment, systemic immunosuppressants, with Cyclosporine-A (CsA) as the treatment choice, have been used as adjunctive therapy in neural transplantation protocols (Sanberg et al., 1994; Freeman et al., 1994; Borlongan et al., 1995). Arguably, systemic CsA treatment may be contraproductive to successful graft acceptance in the CNS because of its systemic effect and because CsA itself has been shown to cause detrimental side effects and may, in fact, be cytotoxic to neural tissues (Berden et al., 1985; de Groen et al., 1984).

It would be desirable to enhance the productive cell transplantation techniques already utilized for neurodegenerative disorders, such as Parkinson's disease, and other types of disorders in ways which would more effectively slow the neurodegenerative disease process, more actively promote the re-establishment of normal neural tissue physiology and better alleviate the functional disabilities associated with the neural tissue dysfunction.

Cell transplantation therapies are optimized by the availability of cryopreserved cells which have high viability. Transplantable cells, such as fetal brain cells, do not withstand cryopreservation well. Therefore, it would be desirable to have a method for enhancing the preservation and viability of cryopreserved cells in order to optimize the function of the cells and to obtain the resultant benefits to the transplant recipient.

SUMMARY OF THE INVENTION AND ADVANTAGES

In accordance with the present invention, there is provided a method of enhancing the viability of cryopreserved cells including the steps of culturing Sertoli cells in media to produce Sertoli cell pre-conditioned media (SCM), adding the pre-conditioned media to cells to be cryopreserved and then cryopreserving the cells.

In a further embodiment, the method includes the steps of co-culturing Sertoli cells and cells to be cryopreserved and then cryopreserving the cells.

Also in accordance with the present invention, there is provided a medium for enhancing the viability of cryopreserved cells. The medium is generated by the steps of culturing Sertoli cells in media to produce Sertoli cell pre-conditioned medium (SCM) and removing the SCM from the Sertoli cells.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
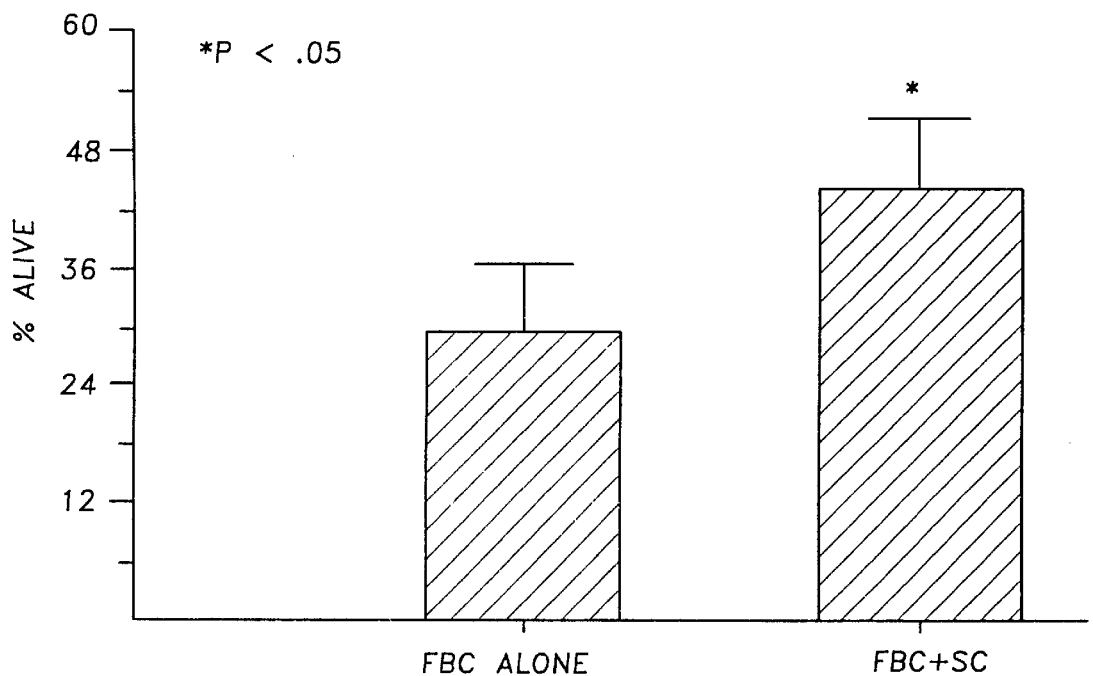
FIG. 1 is a graph illustrating the percent increase of post thaw cryopreserved live fetal brain cells (FBC) and hNT cells maintained in SCM, and FBC isolated from the rat ventral mesencephalon following cryopreservation wherein some FBC's were prepared for cryopreservation in control medium (FBC's alone) and some were cryopreserved with Sertoli cells (FBC+SC) and the number of FBC and live vs. dead estimates were made one hour following thawing.

The present invention provides methods for enhancing the viability of cryopreserved cells by culturing Sertoli cells or Sertoli cell pre-conditioned medium with the cells to be cryopreserved. Alternatively, the method of the present invention provides for adding the preconditioned medium to cryopreserved cells upon thawing.

Enhanced viability describes the ability of cells to survive and function normally following a sustained period of cryopreservation. This can also be referred to as post-thaw viability. That is, cells which are harvested and cryopreserved for later use for purposes including transplantation, can be thawed and a greater percentage of the cells will be alive and viable retaining their original functions. For example, differentiated, non-dividing cells can be harvested for transplantation, cryopreserved according to the present invention, and thawed resulting in a substantially greater percentage of live cells than by previous methods of cryopreservation.

By cryopreserved or cryopreservation, it is meant that the cells are stored at temperatures which are low enough to prevent normal biological functions from occurring. Generally this temperature is at least −70° C. and lower under liquid nitrogen. At these low temperatures, biological degradation of the cells is inhibited thereby preserving the functions of the cells. However, as described above, the prior art methods of cryopreserving cells result in a substantial proportion of cells failing to survive or be viable following cryopreservation. Typically, cryopreservation involves storing cells in a medium which may contain DMSO or an equivalent at very low temperatures by refrigeration or storage under liquid nitrogen or other types of cooling, as known to those skilled in the art.

In the present invention, the medium is prepared by culturing Sertoli cells in a suitable culture medium (incubation medium) as described herein. Isolated Sertoli cells are cultured in incubation medium from one hour to seven days and at a density of $1 \times 10^5$ to $1 \times 10^8$ cells/cm$^2$ at 39° C. with 5%$CO_2$-95% air. In a preferred embodiment the isolated Sertoli cells are cultured in incubation media for 48 hours at a density of $5 \times 10^6$/cm$^2$ and at 39° C. with 5%$CO_2$-95% air.

Following incubation of the Sertoli cells in the incubation medium, the medium (SCM) is deemed "preconditioned". That is, following the preconditioning of the medium, the medium contains nutritional, immunosuppressive, and other factors from Sertoli cells defined herein as trophic factors which enhance not only the viability of cryopreserved cells, but which imparts enhanced growth characteristics to the cells which have been cryopreserved in the medium. The Sertoli cells can be removed from the preconditioned media of the present invention following the culturing of the Sertoli cells therein, or, can be left in the preconditioned media to further enhance the cells to be cryopreserved. Additionally, the cells to be cryopreserved can be co-cultured with the Sertoli cells prior to cryopreservation. Furthermore, the preconditioned medium containing the trophic factors can be added to other media for cell culturing and cryopreservation.

The cells which may be cryopreserved with Sertoli cells or in SCM, according to the present invention, include but are not limited to cells of the peripheral and central nervous system including neural cells, lymphocytes, hybridomas, fibroblasts, cells for gene therapy, fetal cells from various tissues, myoblasts, hepatocytes, endocrine cells, endothelial cells and the like.

As shown in the Examples herein below, the cells preserved in accordance with the present invention can be transplanted into the CNS (brain) to replace dysfunctional cells and when co-transplanted with Sertoli cells, can avoid being rejected. Such a protocol results, therefore, in increased cell survival and cell functional integration with the host tissue. This then will promote re-establishment of normal neural tissue function and thereby ameliorate the behavioral and functional deficits associated with the neurological and/or neurodegenerative disorder being treated.

However, the method of the present invention can also be utilized with other transplantable cells from tissues other than CNS cells such as endocrine cells, muscle cells, and other cells by utilizing similar techniques as those described for neural cells. Furthermore, the method of the present invention may be used for enhancing the outcomes of cell transplant, such as myoblast transplants and cells for gene therapy, by providing such cells with enhanced viability and tropic support for transplant. That is, Sertoli cells and the trophic factors which they produce and/or secrete into the preconditioned media are used to facilitate transplant survival and graft function of the cells being transplanted.

The present invention provides in one embodiment for the co-culturing of Sertoli cells and a second cell type to be cryopreserved in media and cryopreserving the co-cultured cells together. Upon thawing, the Sertoli cells are therefore present and would be co-transplanted with the second cell type. Such a co-cellular transplant provides additional advantages.

Sertoli cells provide local immunosuppression by secreting an immunosuppressant agent, so that there would be no successful antibody or cellular immunological attack waged against the transplanted cells, including the Sertoli cells themselves. Additionally, since the immunosuppression is local and by a biologically tolerable agent, the side effects associated with both systemic immunosuppression and cytotoxicity of agents such as CsA would be avoided. Hence, Sertoli cell co-transplantation provides a significant improvement over the use of systemic immunosuppression with CsA as the necessary adjunctive therapy to neural transplantation as shown in the example below.

The localized immunosuppression by a Sertoli cell-derived immunosuppressant agent can facilitate the survival of both cellular xenografts and allografts. With allografts, co-transplantation with Sertoli cells should provide localized immunosuppression so as to eliminate the need for systemic immunosuppression. With xenografts, co-transplantation with Sertoli cells can provide sufficient local immunosuppression so as to eliminate the need for systemic immunosuppression or the Sertoli cells may be used in combination with a systemic immunosuppressant at a lower dose to prevent rejection. When co-transplanted, the Sertoli cells not only provide local immunosuppression but provide trophic support (i.e. regulatory, nutritional and other factors) to the co-transplanted cells (i.e. the graft). Therefore, the Sertoli cells will not only provide inhibition of the immune response, but will allow enhanced growth and viability of allografts and xenografts by concomitant trophic support.

The source of Sertoli cells is by primary cell isolation from the mammalian testis. The protocol for harvesting the cells is well-defined (Cameron and Muffle, 1991; Griswold, 1992) and considered a routine methodology. Although rat Sertoli cells are utilized in the following examples and have been in a published report (Selawry and Cameron, 1993), it is contemplated that the method of the present invention can be used with Sertoli cells from any suitable mammalian source. A preferred source of Sertoli cells for use with mammals, such as humans, are porcine Sertoli cells. However, if available and suitable, human Sertoli cells may be utilized.

In one embodiment, the Sertoli cells are co-transplanted with the selected neural tissue or other appropriate tissue into the CNS by intracranial infusion (Sanberg et al., 1995).

The source of neural cells for transplantation depends on the neurological disorder being treated. For example, Parkinson's disease is treated with ventral mesencephalic tissue (Lindvall et al., 1990) or chromaffin cells (Lindvall et al., 1987), Huntington's disease is treated with striatal lateral eminence cells (Isacson et al., 1986) and neurological pain is treated with adrenal chromaffin cells (Sagen et al., 1993). Other cell types experimentally transplanted into specific animal models of human neurodegenerative disorders are summarized elsewhere (Dunnett and Bjorklund, 1994) and provide detailed descriptions of cell isolation and transplantation methods. Other non-neural cells that have been transplanted are generally reviewed by Sanberg (1992) and provide detailed descriptions of cell isolation and tranplantation methods.

The following examples demonstrate the media and methods of use of the present invention as well as efficacy for enhancing the availability of viable, cryopreserved cells.

EXAMPLES

GENERAL METHODS

Isolation and Pretreatment of Sertoli Cells

As previously described (Cameron and Muffly, 1991) decapsulated rat testes were subjected to sequential enzymatic treatment at 37° C. using 0.25% trypsin (Sigma) and 0.1% collagenase (Sigma, type V) (Cameron et al. 1987a; Cameron et al. 1987b). The resulting Sertoli cell aggregates were equally distributed in a volume of 20 ml incubation medium into 75 cm$^2$ tissue culture flasks (Costar). Plated Sertoli aggregates were incubated at 39° C. in 5% $CO_2$-95% air for 48 hours which preferentially selects for Sertoli cells over germ cells. After this incubation cells were subjected to hypotonic treatment with sterile 0.5 mM Tris-HCl buffer for one minute (Galdieri et al. 1981) to expedite the removal of contaminating germ cells. Following two washes with incubation medium, flasks were replenished with 20 ml incubation medium and returned to the $CO_2$-injected incubator at 37° C. in 5% $CO_2$-95% air. The resulting pre-treated Sertoli-enriched monocultures contained greater than 95% Sertoli cells. Plating density of <2.0×10$^6$ Sertoli cells/cm$^2$ generally did not result in a confluent monolayer of cells.

Incubation Medium and Sertoli Cell Pre-Conditioned Medium

The incubation medium used for Sertoli cell culture and co-culture was Dulbecco's Minimum Essential Medium-:Hams F12 Nutrient Medium (Whittaker Bioproducts) mixed 1:1 and supplemented with 3 mg/ml L-glutamine (Sigma, grade III), 0.01 cc/ml insulin-transferrin-selenium (ITS, Collaborative Research, Inc.), 50 ng/ml retinol (Sigma), 19 μl/ml lactic acid (Sigma) and 0.01 cc/ml gentamicin sulfate (Gibco).

Following the first 48 hour incubation period of isolated Sertoli cells, media was collected and centrifuged at 1500 rpm for five minutes. The supernatent was collected and immediately frozen in sterile test tubes. This medium was identified as Sertoli pre-conditioned medium (SCM).

EXAMPLE 1

Enhanced Viability of Cryopreserved Cells and Tropic support of Fetal Brain Cells Cell transplantation therapies are optimized by the availability of cryopreserved cells which have high post-thaw viability. Fetal brain cells are not cryopreserved well. To enhance the post-thaw recoverability and viability of fetal brain cells (FBC), the cryoprotectant properties of Sertoli cells and Sertoli cell pre-conditioned medium (SCM) on rat fetal brain cells (FBC) including ventral mesencephalon, commercially available immature brain cells (hNT) and lateral and medial eminence cells were investigated.

Fetal brain cells (FBC) were collected from the ventral mesencephalon of fetal rats (15–17 days gestation). The fetal brain tissue was suspended in medium and initially dispersed by passing it through a series of sequentially decreasing sized hypodermic needles (18–26 gauge). The resulting suspension was treated with 0.1% trypsin for five minutes and followed by 0.1% trypsin inhibitor for two minutes. The suspended FBC were washed (3×), resuspended in incubation medium and plated in poly-L-lysine-coated culture vessels. The hNT cells were acquired commercially.

Figure 2A:
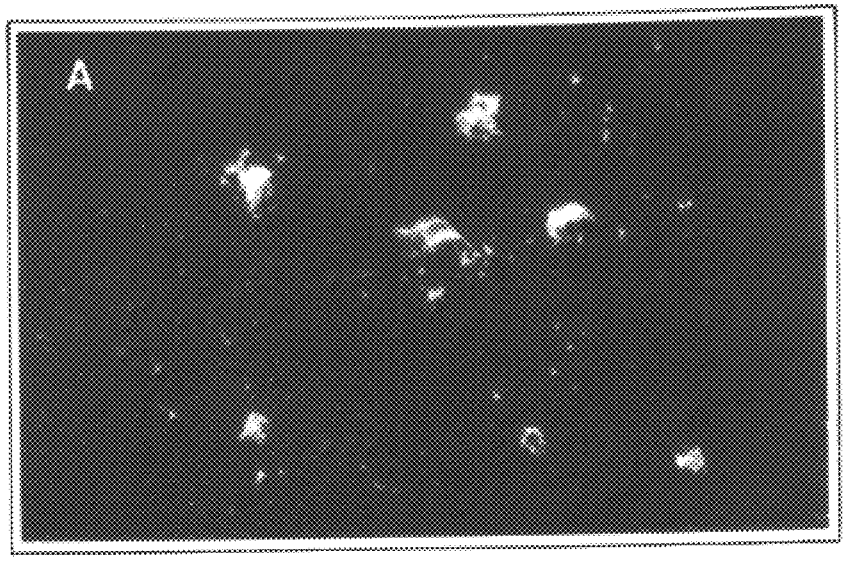
FIGS. 2A–C are light interference micrographs illustrating cells from the ventral mesencephalon of fetal rats (VM) isolated and cultured for seven days in control medium (CM) or Sertoli cell pre-conditioned medium (SCM) and photographed with darkfield, interference contrast optics, wherein (A) depicts VM cells incubated in CM showing no evidence of stimulation or differentiation,(B) depicts VM cells incubated in SCM appearing highly stimulated, and (C) at higher magnification, depicts VM cells incubated in SCM exhibiting neurite outgrowth.
Figure 2B:
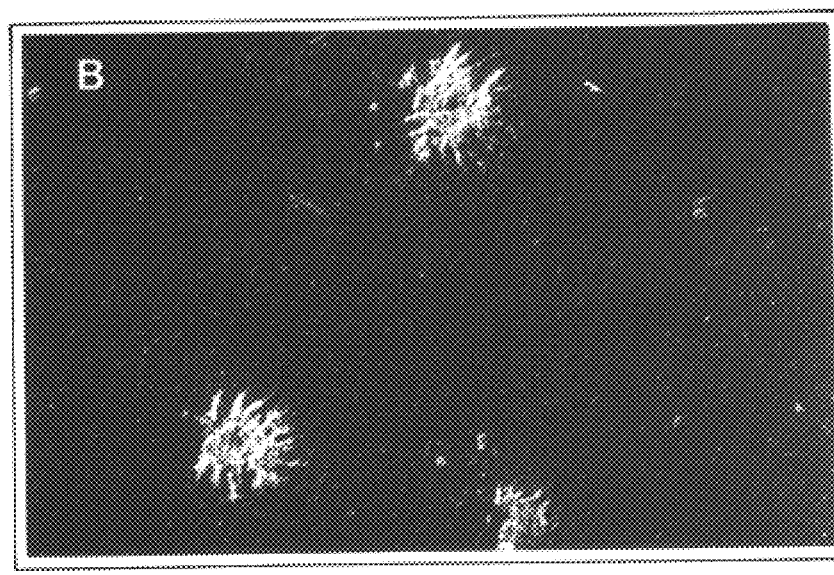
Figure 2C:
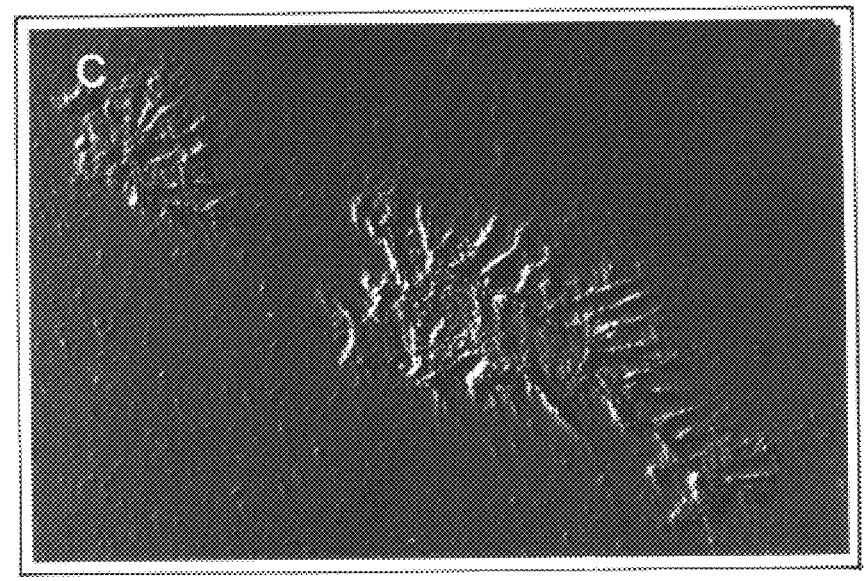

Cells from the ventral mesencephalon of fetal rats (VM) were isolated and either cryopreserved with Sertoli cells (SC) or incubated in Sertoli cell preconditioned medium (SCM) following thawing. The hNT cells were also maintained in SCM after thawing. Both treatments enhanced post-thaw viabilities as shown in FIG. 1. Referring to FIG. 2B, VM cells incubated in SCM were highly stimulated. FIG. 2C illustrates that at higher magnification, VM cells incubated in SCM show neurite outgrowth.

Monocultures of FBC and hNT cells (approximately $5 \times 10^6$/ml) were frozen at high density in SCM+10% DMSO or control medium+10% DMSO and stored in liquid nitrogen. Quickly thawed cells were washed and resuspended in warm SCM. Samples were collected for cell number and live/dead % estimations by duplicate, blind counts by three separate individuals. The percent of post-thaw live cells, estimated by vital dye exclusion, doubled for FBC and hNT cells frozen in SCM when compared to cells frozen in control medium. The mean post-thaw hNT cells recovered from SCM medium ($2.0 \times 10^6$/ml) was significantly ($P<0.05$) greater than the mean post-thaw hNT recovered from control medium ($1.4 \times 10^6$/ml) (See FIG. 1). The results show that media soluble factors secreted by Sertoli cells enhanced the post-thaw viability of FBC, and hNT cells as shown in FIG. 1 and the following Table.

| PERCENT INCREASE OF VIABILITY OVER CONTROLS | |
|---|---|
| FBC + SCM | 10% |
| hNT + SCM | 43% |

EXAMPLE 2

SURVIVAL OF SERTOLI CELLS IN THE BRAIN

Transplantation of Sertoli cell/chromaffin cell co-graphs into the striatum of the brain using methods described herein.

Figure 3A:
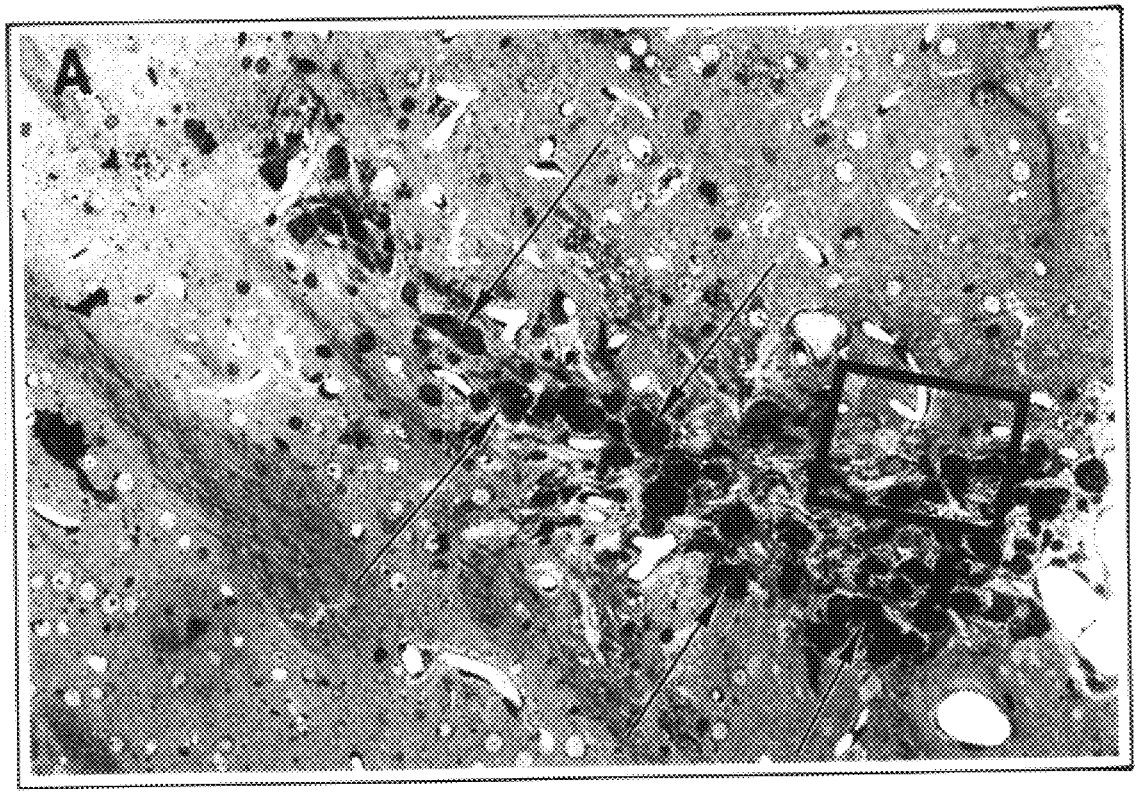
FIGS. 3A–B are micrographs illustrating the cellular structure and tissue architecture of the Sertoli cell/chromaffin cell co-grafts in the striatum of the brain, wherein (A) depicts electron dense chromaffin cells (arrows) easily identified because of the inclusion of secretory granules unique to these cells, and (B) shows the boxed area in (A) at higher magnification, with higher resolution, Sertoli cells (arrows) are seen immediately adjacent to the electron dense chromaffin cells.
Figure 3B:

FIG. 3A illustrates that the transplanted chromaffin cells (arrows, electron dense) were present and easily identified because of the inclusion of secretory granules unique to the cells. FIG. 3B shows the boxed area in FIG. 3A at a higher magnification, wherein at a higher resolution, co-transplanted Sertoli cells (arrows) were detected immediately adjacent to the electron dense chromaffin cells. This demonstrates the survival of co-grafted adrenal chromaffin cells with Sertoli cells in the brain.

EXAMPLE 3

Effects of Cyclosporine A (CsA) on the survival of transplanted Sertoli cells

Fluorescent cell labeling: Immediately prior to transplantation (approximately two hours), Sertoli cell monocultures prepared as described herein were treated with CM-DiI fluorescent dye for cell tracking (100(1 stock/ml medium; Molecular Probes, Inc., Eugene, Oreg.) for seven minutes at 37° C. and then placed in the refrigerator (4° C.) for an additional 15 minutes. Fluorescent "tagged" Sertoli cells were washed (three times) and resuspended in 1 ml of incubation medium.

Figure 4A:
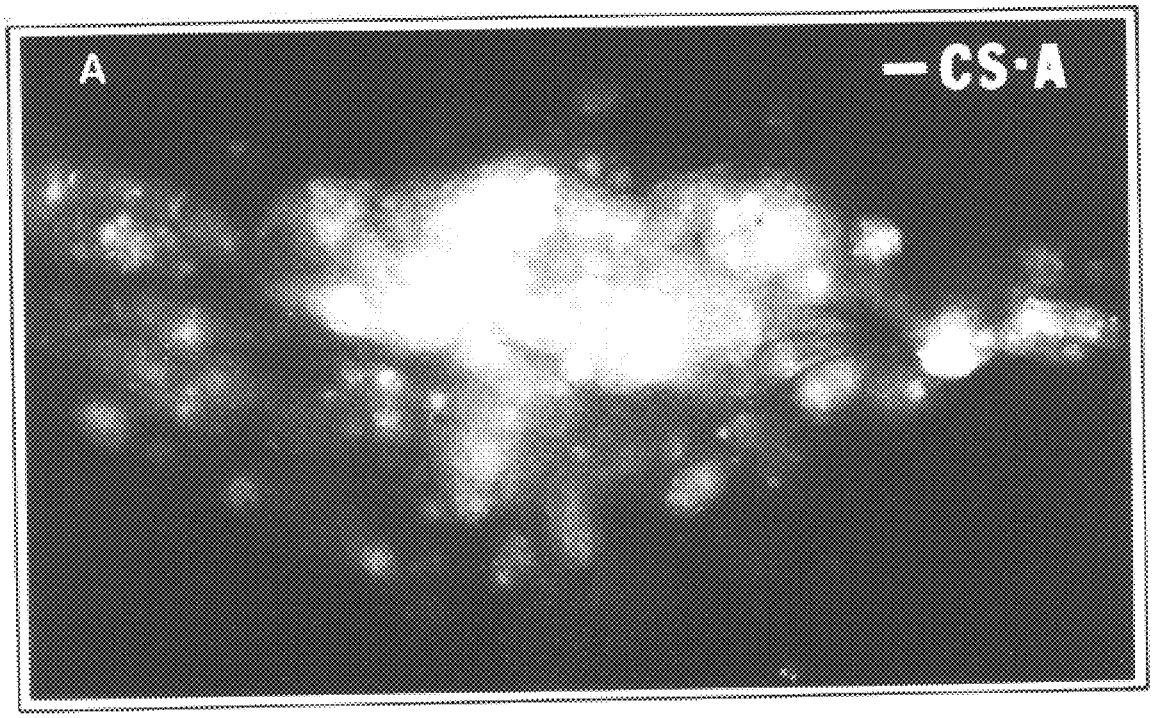
FIGS. 4A–B are light micrographs illustrating grafted Sertoli cells in situ labeled with a florescent tag (DiI) prior to their transplantation into the striatum of the brain wherein (A) depicts viable, florescent Sertoli cells in a rat host that had not received immunosuppression therapy with Cyclosporine A (CsA), and (B) shows viable, florescent Sertoli cells in the rat host that had received CsA immunosuppression therapy, no difference is apparent in the viability of grafted Sertoli cells between immunosuppressed and non-immunosuppressed hosts.
Figure 4B:
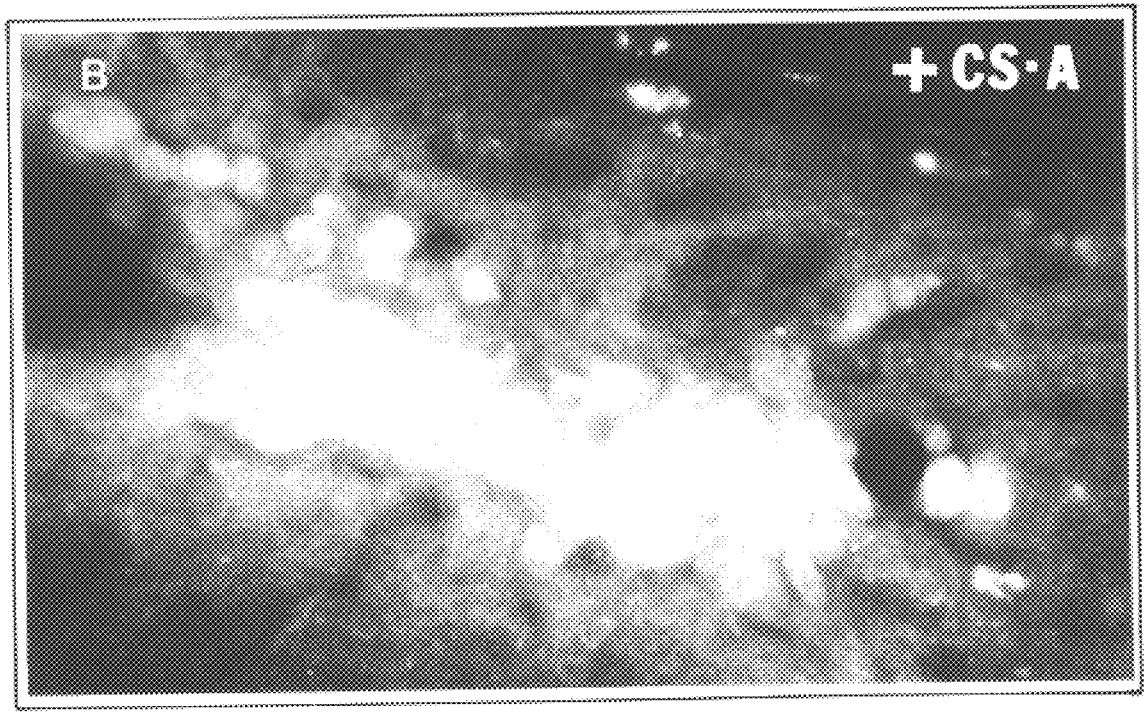

The effect of cyclosporine A on the survival of grafted Sertoli cells in situ was examined. Grafted Sertoli cells were labeled with a fluorescent tag (DiI) prior to transplantation into the striatum of the brain. The tissue was collected one month post-transplantation. Referring to FIG. 4A, viable fluorescent Sertoli cells were seen in a rat host that had not received immunosuppression therapy with cyclosporine A. Referring to FIG. 4B, viable fluorescent Sertoli cells are shown in a rat host that did receive cyclosporine A immunosuppression therapy. This example demonstrates that cyclosporine A is not necessary for the survival of Sertoli cells transplanted into the brain.

Throughout this application various publications are referenced by citation. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

REFERENCES CITED

Berden et al., "Severe central nervous system toxicity associated with cyclosporine" Lance 26:219–220 (1985).

Bjorklund and Stenevi, "Intracerebral neural grafting: a historical perspective" in Bjorklund, A. and U. Stenevi, eds. Neural grafting in the mammalian CNS, Amsterdam: Elsevier, 3–11 (1985).

Bjorklund, "Dopaminergic transplants in experimental Parkinsonism: Cellular mechanisms of graft-induced functional recovery" Current Biology, 2:683–689 (1992).

Borlongan et al., "Cyclosporine-A increases spontaneous and dopamine agonist-induced locomotor behavior in normal rats" Cell Transplant., 4:65–73 (1995).

Borlongan et al. "PR: Systemic 3-nitropropionic acid: Behavioral deficits and striatal damage in rats", Brain Research Bulletin, 36:549–556 (1995).

Cameron et al., "Successful islet/abdominal testis transplantation does not require Leydig cells" Transplantation, 50:649–653 (1990).

Cameron and Muffly, "Hormonal regulation of spermated binding to Sertoli cells in vitro" J.Cell Sci., 100:532–533 (1991).

de Groen et al., "Central nervous system toxicity after liver transplantation" N. Engl. J. Med. 14:861–866 (1984).

Dunnett and Bjorklund, Functional Neural Transplantation, Advances in Neuroscience, Volume 2, Raven Press, New York.

Freeman et al., "The USF protocol for fetal nigral transplantation in Parkinson's disease" Experimental Neurology, 129:6–7 (1994).

Griswold, "Protein secretion by Sertoli cells: general considerations" in Russel, L. D. and M. D. Griswold, eds. The Sertoli Cell, Cache River Press, Clearwater, Fla., 195–200.

Isacson et al., "Graft-induced behavioral recovery in an animal model of Huntington's disease" Proc. Natl. Acad. Sci., 83:2728–2732 (1986).

Koutouzis et al., "PR: Systemic 3-nitropropionic acid: Long term effects on locomotor behavior" Brain Research, 646:242–246 (1994).

Lindvall et al., "Transplantation in Parkinson's disease: two cases of adrenal medullary grafts to the putamen" Ann. Neurol., 22:457–468 (1987).

Lindvall et al., "Grafts of fetal dopamine neurons survive and improve motor function in Parkinson's disease" Science, 247:574–577 (1990).

Pakzaban et al., "Increased proportion of Ache-rich zones and improved morphological integration in host striatum of fetal grafts derived from the lateral but not the medial ganglionic eminence" Exp. Brain Res., 97:13–22 (1993).

Paxinos and Watson, "The rat brain in stereotaxic coordinates" Sydney, Academic Press (1984).

Sagen et al., "Transplants of immunologically isolated xenogeneic chromaffin cells provide a long-term source of pain-reducing neuroactive substances" J. Neurosci. 13:2415–2423 (1993).

Sanberg, (Editor-in-chief) "Cell Transplantation", Elsevier Science Publishers, New York, 1992-Present.

Sanberg et al., "Cell transplantation for Huntington's disease" R. G. Landes Co., Boca Raton, Fla., pp. 19–21 (1994).

Sanberg et al., "Sertoli cells induce immunoreactivity and functional recovery following transplantation into the striatum of 6-OHDA lesioned rats (in preparation) (1995).

Selawry and Cameron, "Sertoli cell-enriched fraction in successful islet cell transplantation" Cell Transplant., 2:123–129 (1993).

Wictorin et al., "Reformation of long axon pathways in adult rat CNS by human forebrain neuroblasts" Nature, 347:556–558 (1990).

We claim:

1. A medium for enhancing the viability of cryopreserved cells, said media generated by the steps of:
    culturing Sertoli cells in a medium consisting essentially of Dulbecco's minimum essential medium and Hams F12 nutrient medium mixed 1:1 and supplemented with three milligrams per milliliter L-glutamine, 0.01 cc per ml insulin-transferrin-selenium, 5 ng per ml retinal, 19 microliter per ml lactic acid and 0.01 cc per ml gentamicin sulfate to produce a preconditioned medium.

2. A medium as set forth in claim 1, further including the step of removing the preconditioned medium from the Sertoli cells.

3. A medium as set forth in claim 1, wherein said culturing step is further defined as culturing the Sertoli cells for a period of time ranging from one hour to seven days.

4. A medium as set forth in claim 3, wherein the time period is 48 hours.

5. A medium as set forth in claim 1, wherein the concentration of the Sertoli cells ranges from $1\times10^5$ cells/cm$^2$ to $1\times10^8$ cells/cm$^2$.

6. A medium as set forth in claim 5, wherein the concentration is $5\times10^6$ cells/cm$^2$.

* * * * *